(12) United States Patent
Ren et al.

(10) Patent No.: US 11,648,374 B2
(45) Date of Patent: May 16, 2023

(54) SURFACE TOPOGRAPHY WITH FERROMAGNETIC POLYMER PILLARS CAPABLE OF MOVEMENT IN RESPONSE TO MAGNETIC FIELDS

(71) Applicants: Dacheng Ren, Manlius, NY (US); Huan Gu, Syracuse, NY (US)

(72) Inventors: Dacheng Ren, Manlius, NY (US); Huan Gu, Syracuse, NY (US)

(73) Assignee: SYRACUSE UNIVERSITY, Syracuse, NY (US)

( * ) Notice: Subject to any disclaimer, the term of this patent is extended or adjusted under 35 U.S.C. 154(b) by 1077 days.

(21) Appl. No.: 16/249,532

(22) Filed: Jan. 16, 2019

(65) Prior Publication Data

US 2019/0217349 A1   Jul. 18, 2019

Related U.S. Application Data

(60) Provisional application No. 62/618,320, filed on Jan. 17, 2018.

(51) Int. Cl.
| | |
|---|---|
| *A61M 25/00* | (2006.01) |
| *B81C 1/00* | (2006.01) |
| *A01N 25/34* | (2006.01) |
| *A01N 59/16* | (2006.01) |
| *B08B 17/06* | (2006.01) |
| *B29C 33/00* | (2006.01) |
| *B29C 35/02* | (2006.01) |
| *B82Y 5/00* | (2011.01) |

(Continued)

(52) U.S. Cl.
CPC ......... *A61M 25/0043* (2013.01); *A01N 25/34* (2013.01); *A01N 59/16* (2013.01); *B08B 17/065* (2013.01); *B29C 33/0027* (2013.01); *B29C 35/02* (2013.01); *B81C 1/00206* (2013.01); *B81C 1/00214* (2013.01); *A61M 2025/006* (2013.01); *A61M 2025/0019* (2013.01); *A61M 2025/0058* (2013.01); *A61M 2205/0272* (2013.01); *B29K 2105/203* (2013.01); *B29K 2995/0008* (2013.01); *B81B 2207/053* (2013.01); *B82Y 5/00* (2013.01); *B82Y 30/00* (2013.01)

(58) Field of Classification Search
CPC .............. A61L 242/04; A61L 2400/18; A61M 2025/006; A61M 2205/0272; A61M 25/0043; A61M 2025/0058
See application file for complete search history.

(56) References Cited

U.S. PATENT DOCUMENTS

| | | | |
|---|---|---|---|
| 2009/0076597 A1* | 3/2009 | Dahlgren | A61F 2/2445 606/53 |
| 2016/0075987 A1* | 3/2016 | Zhang | C12M 35/06 435/395 |

* cited by examiner

*Primary Examiner* — Deanna K Hall
(74) *Attorney, Agent, or Firm* — David L. Nocilly (57) ABSTRACT

An anti-fouling surface having micron scale pillars embedded with $Fe_3O_4$ nanoparticles is designed. The pillars may be repeatedly induced to move according to a predetermined frequency, such as one that mimic that of the beating movement of natural cilia, through the application of a magnetic field. When square-shaped pillars with a height of 10 μm, width of 2 μm, and inter-pattern distance of 5 μm actuated for three minutes, more than 99.9 percent of biofilm cells were detached and via gentle rinsing from the surface having the pillars. The anti-fouling surface enables effective prevention of biofilm formation and removal of established biofilms, and can be applied to a broad spectrum of polymers.

9 Claims, 6 Drawing Sheets

(51) Int. Cl.
*B82Y 30/00* (2011.01)
*B29K 105/20* (2006.01)

SURFACE TOPOGRAPHY WITH FERROMAGNETIC POLYMER PILLARS CAPABLE OF MOVEMENT IN RESPONSE TO MAGNETIC FIELDS

CROSS-REFERENCE TO RELATED APPLICATIONS

The present application claims priority to U.S. Provisional App. No. 62/618,320, filed on Jan. 17, 2018.

BACKGROUND OF THE INVENTION

1. Field of the Invention

The present invention relates to anti-fouling surfaces and, more particularly, to magnetically driven artificial cilia that can remove bacterial biofilms from a surface.

2. Description of the Related Art

Biofilms are surface-attached communities of microorganisms that are highly resistant to antimicrobials and disinfectants, causing persistent problems such as chronic infections in humans and biofouling and biocorrosion in industrial settings. The adverse effects of biofilms on both the economy and public health have stimulated extensive biofilm research. However, long-term biofilm control—especially the removal of established biofilms—remains difficult.

To address this challenge, micron scale topography has been designed using biocompatible shape memory polymers (SMPs). The results demonstrated that mature biofilms can be effectively removed (up to 99.9% in minutes) by on-demand triggering of changes in surface topography. This method was found effective against biofilms of both Gram-negative and Gram-positive bacteria, demonstrating the potential of dynamic topography in biofilm control. However, the shape change of most biocompatible SMPs can only occur once, limiting the long-term application of this technology. Accordingly, there is a need in the art for a surface design that can be used to assist with the removal of biofilms in repeating cycles.

BRIEF SUMMARY OF THE INVENTION

The present invention comprises a surface topography that mimics the natural anti-fouling strategies of the beating cilia that protect higher organisms from infection by bacterial pathogens, but with tailored mechanical properties to work in the absence of mucin. More specifically, the present invention may be a surface having an anti-fouling topography comprising a plurality of pillars formed from a polymer and extending from a substrate to define a corresponding plurality of free ends along with a plurality of magnetic particles disposed in each of the plurality of pillars such that the magnetic particles are more highly concentrated in the free ends of each of the plurality of pillars. The substrate may comprise a catheter having a wire extending therethrough. The wire may extend helically through the catheter. The wire may be coupled to a power source and be configured to produce a magnetic field that will encompass the plurality of pillars. The power source may include an oscillator that is configured to provide a pulsed direct current output to the wire. The magnetic particles may comprise superparamagnetic iron oxide nanoparticles and the polymer may comprise poly(dimethylsiloxane). The plurality of pillars may have a height of 10 μm, and width of 2 μm. The plurality of pillars may be disposed in a predetermined uniform pattern having an inter-pattern distance of 5 μm. The plurality of pillars may be square in cross-section.

The present invention also comprises a method of making an anti-fouling topographic surface. The steps of the method include providing a mixture containing at least one monomer, adding a plurality of magnetic particles to the mixture, pouring the mixture containing the plurality of magnetic particles to a mold defining a plurality of pillars having a corresponding plurality of free ends, migrating the magnetic particles to the plurality of free ends, polymerizing the monomer of the mixture containing the plurality of magnetic particles to form a polymer with entrapped magnetic particles, and removing the polymerized polymer containing the plurality of magnetic particles from the mold to provide a plurality of pillars formed from the polymer containing the plurality of magnetic particles. The step of migrating the magnetic particles to the plurality of free ends may comprise the step of applying a magnetic field. The step of migrating the magnetic particles to the plurality of free ends may comprise the step of using gravity. The substrate may comprise a catheter and the plurality of pillars extending from an inner/outer surface of the catheter. The method may further include step of embedding a wire in the catheter. The wire may be embedded helically through the catheter. The method may also include the step of coupling the wire to a power source and applying current to the wire to produce a magnetic field that encompasses the plurality of pillars so that the plurality of pillars move. The magnetic particles may comprise superparamagnetic iron oxide nanoparticles. The polymer may comprises poly(dimethylsiloxane). Each of the plurality of pillars may have a height of 10 μm and width of 2 μm and are disposed in a predetermined uniform pattern having an inter-pattern distance of 5 μm.

As an example, systematically designed poly(dimethylsiloxane) (PDMS) surface topographies filled with biocompatible superparamagnetic $Fe_3O_4$ nanoparticles may be actuated with a programmed external magnetic field (5 mT) to mimic the beating of human motile cilia. These dynamic surface topographies were embossed onto PDMS surfaces to engineer a "living" surface with long-term antifouling effects. The antifouling properties of these surfaces were first validated against 48 h *Pseudomonas aeruginosa* PAO1 biofilms preformed before actuation. By actuating the dynamic square-shaped surface topographies with a height of 10 μm, width of 2 μm, and inter-pattern distance of 5 μm for 3 min, more than 99.9% biofilm cells were detached and removed by gentle rinsing. Release of nanoparticles from the pillars was negligible and no cytotoxicity to mammalian cells were observed. The biocompatibility and potent anti-fouling effects of these surfaces may be used for biomedical applications and thus represent a new generation of anti-fouling surfaces that can be programmed remotely through wireless coupling.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
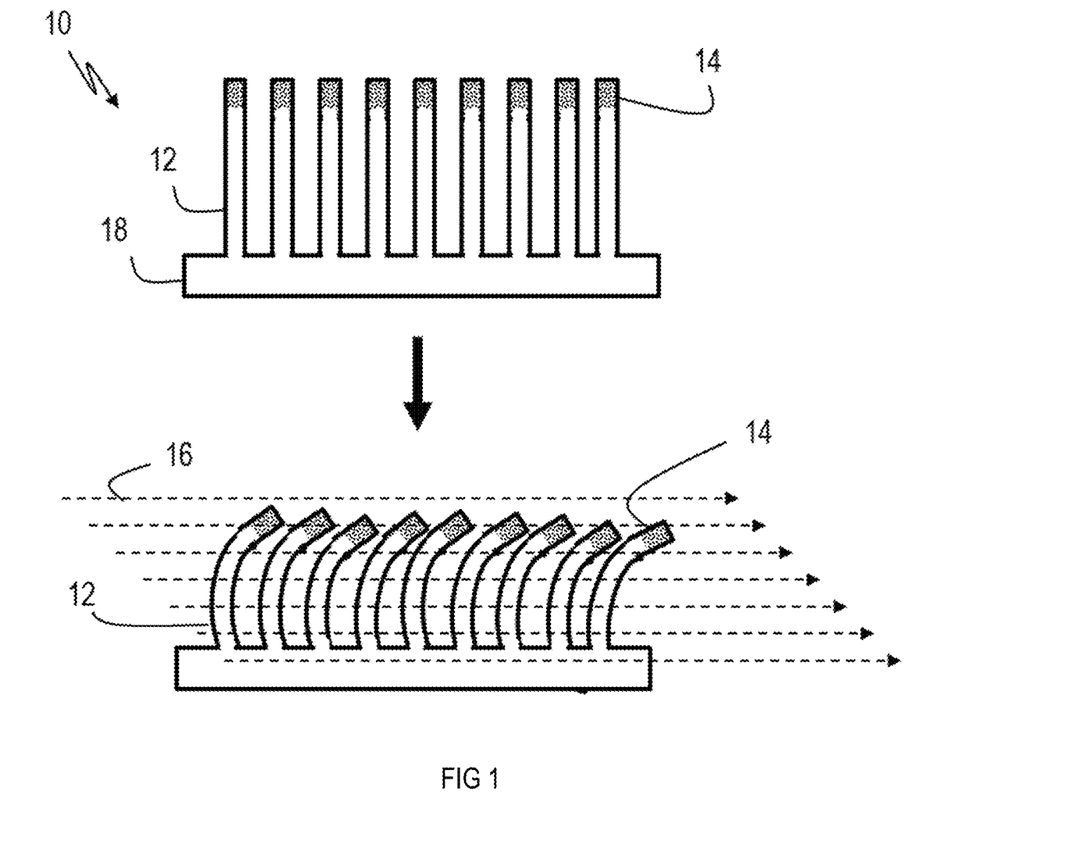
FIG. 1 is a schematic of a surface topography according to the present invention having pillars that can move in response to an applied magnetic field.

Referring to the figures, wherein like numeral refer to like parts throughout, there is seen in FIG. 1 system 10 formed from an engineered material that includes repeatable, dynamic changes in surface topography that mimic the natural anti-fouling strategies of the beating cilia that protect higher organisms from infection by bacterial pathogens in constant contact. More specifically, a plurality of micron scale pillars 12 are formed using a polymer of choice and provided with movement of a desired frequency, e.g., the beating movement of natural cilia, by the use of magnetic particles 14 that are embedded within an end region of each of the plurality of pillars 12. The application of a magnetic field 16 over the plurality of pillars 12 causes movement of the end regions of each pillar 12 due to the presence of magnetic particles 14. It should be recognized that magnetic field 16 may be driven to accomplish any particular movement of pillars 12, such as a field that is applied uniformly over pillars 12 so that all pillars move together or in a manner that propagates from left to right as seen in FIG. 1, or combinations thereof, to mimic the beating of cilia. The presence of the magnetic particles 14 allows pillars 12 to move in response to external magnetic field 16. Magnetic field 16 may be generated with desired strength and frequency either by supplying an electric current through a coiled metal wire around the surface topography, or through wireless coupling. The induced movement of the pillars 12 enables the antifouling activities of an engineered device, whether external or implanted. The use of a coil carrying electric current to induce magnetic field 16 enables more precise and complex control algorithms. Using coils also allows for control remotely through wireless coupling and thus can be applied to implanted medical devices.

Figure 2:
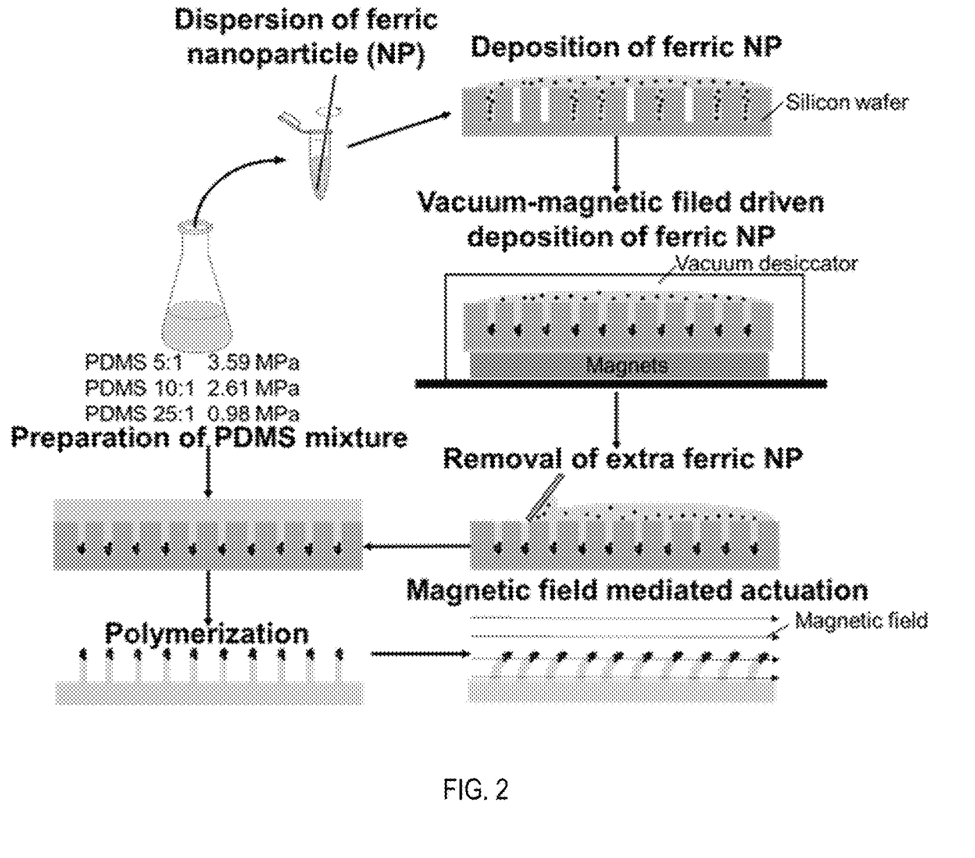
FIG. 2 is a schematic of a method of making a surface topography according to the present invention having pillars that can move in response to an applied magnetic field.

Referring to FIG. 2, the specifically designed surface topography can be created using a molding process with biocompatible superparamagnetic $Fe_3O_4$ nanoparticles used for magnetic particles 14 added into the polymer mixture used to form pillars 12 prior to cross-linking. A vacuum may be used to let magnetic particles 14 settle before the polymer is put in the mold, and the present invention may be used with essentially any polymer that has sufficient flexibility. Height of pillars 12 (10 μm in an example provided herein) from the supporting substrate 18 can vary substantially as well as the overall pillar geometry. For example, a Sylgard® 184 silicone elastomer kit with two components (elastomer base and cure agents) was used to make PDMS surfaces. Using this kit, the stiffness of PDMS surface topographies can be varied by adjusting the weight ratio between elastomer base and cure agent (for example, but not limited to, 5:1, 10:1, or 25:1). The same method can also be used for other polymers. To embed superparamagnetic iron oxide nanoparticles into surface topographies according to the present invention, they are evenly dispersed into PDMS mixtures first. During this process, the concentration of magnetic particles 14 can be controlled by changing the weight ratio between magnetic particles 14 and the PDMS mixture to adjust the subsequent movement of dynamic pillars in response to the magnetic field. The mixture is then poured onto silicon wafers fabricated with systematically designed complementary patterns. To ensure the migration of magnetic particles 14 to the tips of pillars 12, the silicon wafer is transferred into a vacuum desiccator with a magnet positioned at the bottom for one hour. Then, the extra PDMS mixture with magnetic particles 14 on top of the wells is removed before clean PDMS mixture (no magnetic particles 14) is applied onto the silicon wafer as the base of surface topographies. The PDMS surfaces are polymerized at 60° C. for 24 h. By peeling off the PDMS surfaces, dynamic surface topographies are embossed onto PDMS surfaces and result in a pattern of pillars 12 as seen in FIG. 3.

The method of making the anti-fouling surface according to the present invention allows the superparamagnetic iron oxide nanoparticles to be fixed on the tips of surface topographies. This arrangement allows pillars 12 to move with higher flexibility and bending angles compared to the conventional approaches. In addition, using the molding method of the present invention, the dimension of the surface topography can be rigorously controlled with more diversity in shape of pillars 12 and finer control of resolution. In addition to the dimensional control, the molding method of the present invention allows for the application of dynamic surface topographies using a broad spectrum of polymers.

Figure 3:
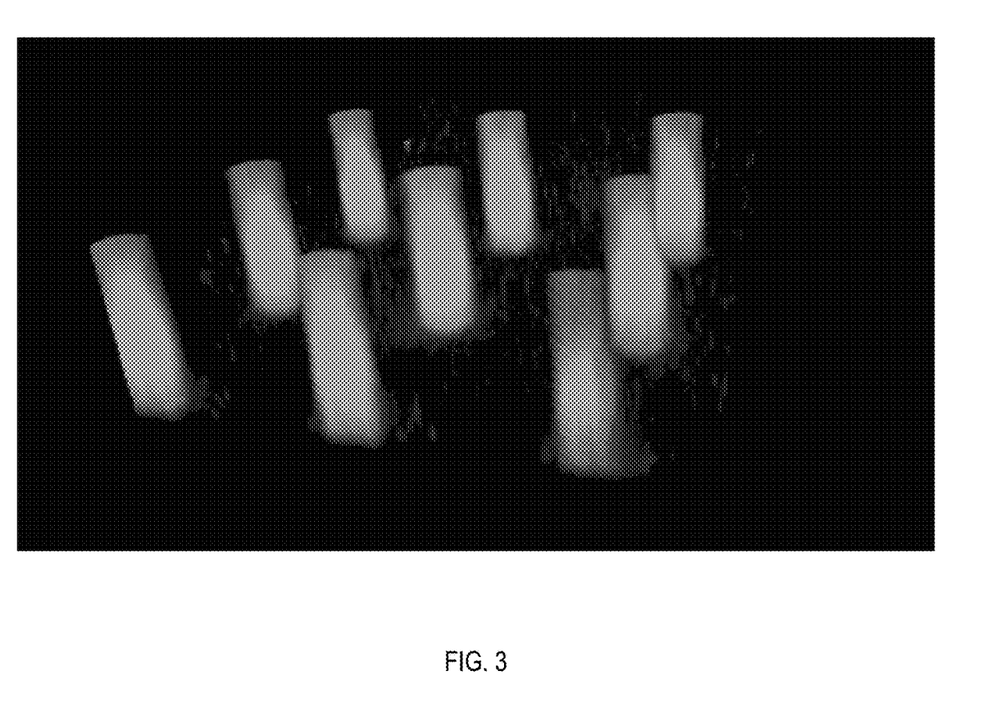
FIG. 3 is an image of a surface topography according to the present invention having pillars that can move in response to an applied magnetic field.
Figure 4:
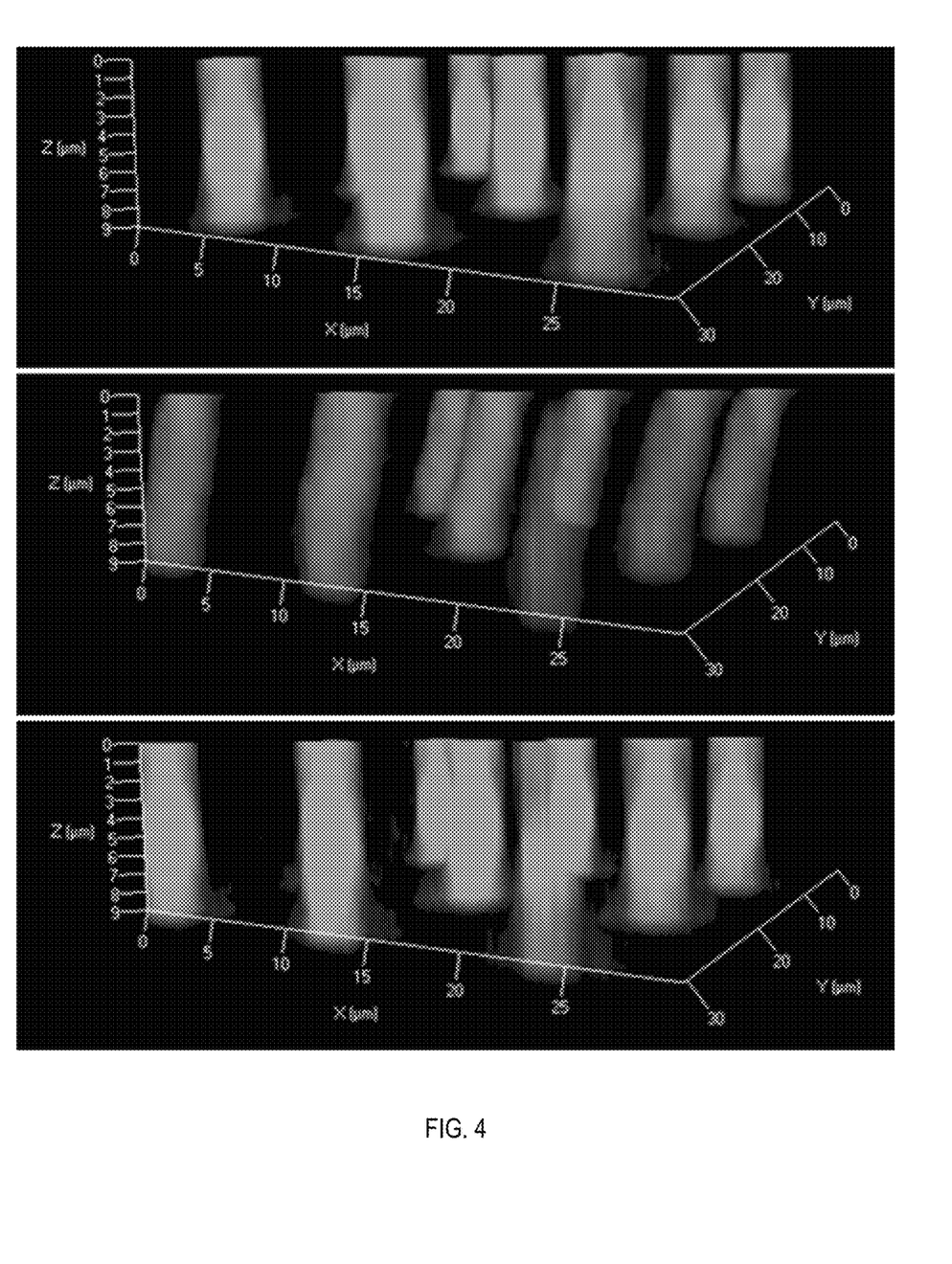
FIG. 4 is a series of images of a surface topography according to the present invention exhibiting ciliary movement in response to an applied magnetic field.

In a demonstration, pillars 12 according to the present invention as seen in FIG. 3 were subjected to an external magnetic field of 5 mT and driven to mimic the rhythmic beating of human motile cilia and imaged to capture the resulting movement, as seen in FIG. 4. It should be recognized that cylindrical or other shapes may be used provided that the general overall dimension are appropriate such that the pillars can be driven to move effectively.

Figure 5:
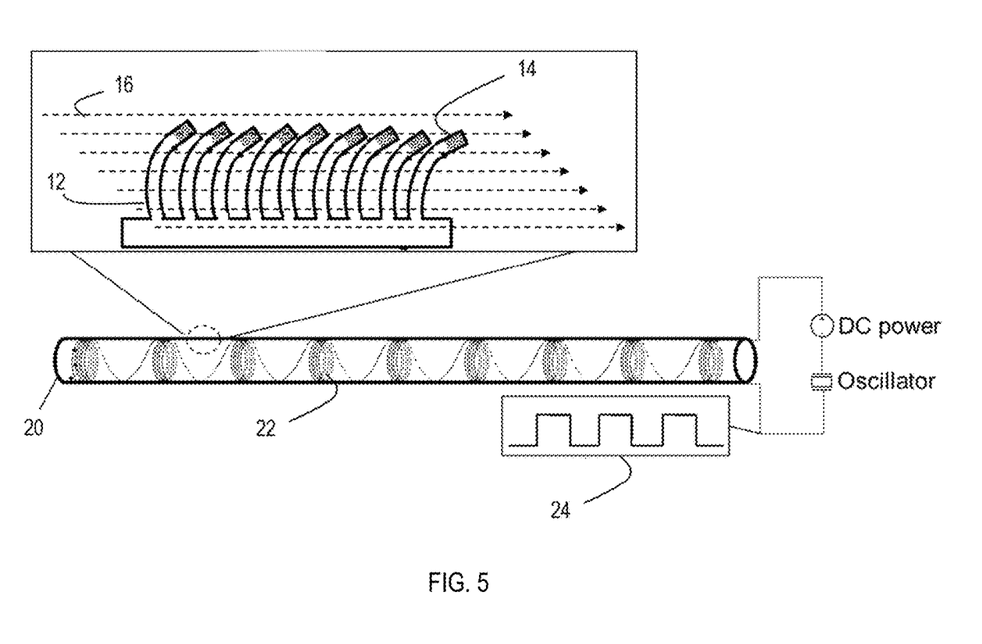
FIG. 5 is a schematic of an exemplary catheter according to the present invention having a surface topography with pillars that can move in response to an applied magnetic field.

Referring to FIG. 5, system 10 of present invention may be incorporated into an exemplary medical device, such as a urinary catheter 20, and provided with pillars 12 that are 10 μm in height and 2 μm in diameter. Pillars 12 are preferably positioned in a predetermined pattern, such as a grid, and spaced 5 μm apart from each other across the inner and outer surfaces of the catheter. As described above, the polymer used to form pillars 12 is loaded with $Fe_3O_4$ nanoparticles as magnetic particles 14. In a first embodiment, catheter 20 is formed from two or more layers of polymer with a thin metal wire (insulated) 22 positioned between the layers and wound around the catheter in a helical fashion so that the magnetic field produced by current in wire 22 will induce movement of pillars 12. A DC power source 24 and oscillator 26 are used to provide a pulsed direct current (DC) output 28 to coiled wire 22, thereby inducing a pulsed magnetic field that causes movement of pillars 12 due to the ferric nanoparticles serving as magnetic particles 14.

Figure 6:
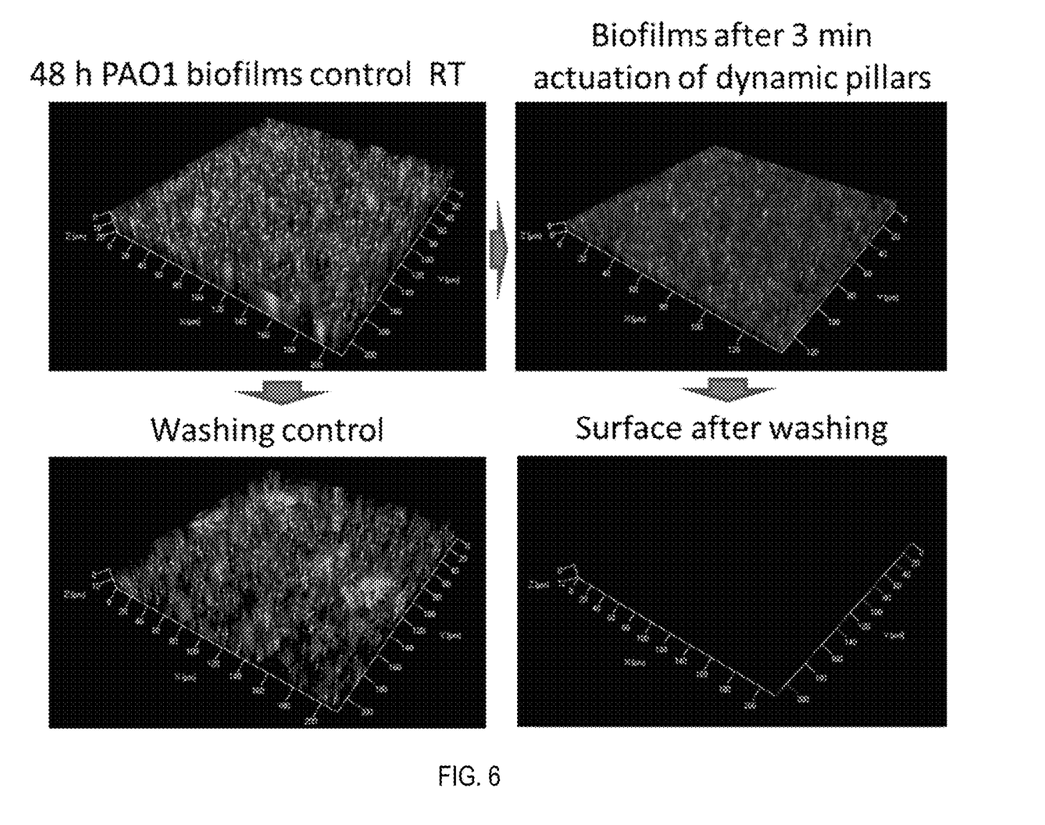
FIG. 6 is series of images demonstrating the anti-fouling capabilities of a surface topography according to the present invention.

There is seen in FIG. 6, testing of catheter 20 formed according to the present invention to have PDMS pillars 12 with ferric nanoparticles serving as magnetic particles 14 located in the tips of pillars 12, such as through the method of making pillars 12 as described above. The antifouling properties of the device having the pillars was validated against 48 h *Pseudomonas aeruginosa* PAO1 biofilms preformed before actuation. When square-shaped surface topographies having pillars with a height of 10 μm, width of 2 μm, and inter-pattern distance of 5 μm were actuated for 3 min, more than 99.9 percent of biofilm cells were detached from the surface and removed by gentle rinsing, as seen in FIG. 6. Release of nanoparticles from the pillars was negligible and no cytotoxicity to mammalian cells was observed.

The biocompatibility and potent antifouling effects of surfaces according to the present invention have applicability in biomedical applications and represent a new category of antifouling surfaces that can be programmed remotely through wireless coupling. Compared to other methods of biofilm control that rely on static or one time changes in surface topography, the present invention allows for repeated dynamic movement that can be programmed as desired. By tailoring the mechanical properties of the pillars and the frequency of movement, strong antifouling effects can be obtained. The present invention may be easily incorporated into essentially any polymer of choice with long-term effect.

The invention claimed is:

1. A surface having an anti-fouling topography, comprising:
    a plurality of pillars formed from a polymer and extending from a substrate of the polymer to define a corresponding plurality of free ends, wherein the substrate comprises a catheter having a wire extending therethrough; and
    a plurality of magnetic particles disposed in each of the plurality of pillars such that the magnetic particles are more highly concentrated in the free ends of each of the plurality of pillars.

2. The surface of claim 1, wherein wire extends helically through the catheter.

3. The surface of claim 2, wherein the wire is coupled to a power source and is configured to produce a magnetic field that will encompass the plurality of pillars.

4. The surface of claim 3, wherein the power source includes an oscillator that is configured to provide a pulsed direct current output to the wire.

5. The surface of claim 4, wherein the magnetic particles comprise superparamagnetic iron oxide nanoparticles.

6. The surface of claim 5, wherein the polymer comprises poly(dimethylsiloxane).

7. The surface of claim 6, wherein each of the plurality of pillars have a height of 10 μm, and width of 2 μm.

8. The surface of claim 7, wherein the plurality of pillars are disposed in a predetermined uniform pattern having an inter-pattern distance of 5 μm.

9. The surface of claim 8, wherein each of the plurality of pillars are square in cross-section.

* * * * *